(12) United States Patent
Kriheli (10) Patent No.: US 11,357,702 B2
(45) Date of Patent: Jun. 14, 2022

(54) LIQUID TRANSFER SYSTEM

(71) Applicant: EQUASHIELD MEDICAL LTD., Tefen Industrial Park (IL)

(72) Inventor: Marino Kriheli, Tel Aviv (IL)

(73) Assignee: EQUASHIELD MEDICAL LTD., Migdal Tefen (IL)

( * ) Notice: Subject to any disclaimer, the term of this patent is extended or adjusted under 35 U.S.C. 154(b) by 337 days.

(21) Appl. No.: 15/516,388

(22) PCT Filed: Oct. 2, 2015

(86) PCT No.: PCT/IB2015/057563
§ 371 (c)(1),
(2) Date: Apr. 1, 2017

(87) PCT Pub. No.: WO2016/051390
PCT Pub. Date: Apr. 7, 2016

(65) Prior Publication Data
US 2017/0246085 A1  Aug. 31, 2017

Related U.S. Application Data

(60) Provisional application No. 62/058,667, filed on Oct. 2, 2014.

(51) Int. Cl.
*A61J 1/20* (2006.01)
*A61M 5/178* (2006.01)
(Continued)

(52) U.S. Cl.
CPC .............. *A61J 1/2058* (2015.05); *A61M 5/14* (2013.01); *A61M 5/1782* (2013.01);
(Continued)

(58) Field of Classification Search
CPC .. A61J 1/20; A61J 1/201; A61J 1/2017; A61J 1/2058; A61J 1/2082; A61M 2039/2493;
(Continued)

(56) References Cited

U.S. PATENT DOCUMENTS 6,582,415 B1   6/2003   Fowles et al.
8,469,940 B2   6/2013   Garfield et al.
(Continued)

FOREIGN PATENT DOCUMENTS

JP    1979-002786      7/1983
WO    PCT/2013/025946 A1   2/2013

*Primary Examiner* — Kai H Weng
(74) *Attorney, Agent, or Firm* — Mark David Torche; Patwrite Law (57) ABSTRACT

Disclosed is a transfer device for use in reconstituting dry drugs and for diluting liquid drugs in drug containers. The transfer device includes a multi-port manifold and a connector suitable to be attached to a drug container, a first conduit to transfer a liquid entering an inlet port of the manifold through the connector and into the drug container, and a second conduit to transfer a gaseous fluid through the connector to an outlet port of the manifold. Also disclosed is a closed liquid transfer system which includes the transfer device, a tube connectable to the inlet port for transporting a liquid to the transfer device, a tube connectable to the outlet port for transporting the gaseous fluid away from the transfer device, and a gas collection container to collect the gaseous fluid in the gas transporting tube.

19 Claims, 6 Drawing Sheets

(51) Int. Cl.
*A61M 39/22* (2006.01)
*A61M 39/24* (2006.01)
*A61M 5/14* (2006.01)

(52) U.S. Cl.
CPC .......... *A61M 39/223* (2013.01); *A61M 39/24* (2013.01); *A61J 1/20* (2013.01); *A61J 1/201* (2015.05); *A61J 1/2017* (2015.05); *A61J 1/2082* (2015.05); *A61M 2039/2493* (2013.01); *A61M 2202/02* (2013.01)

(58) Field of Classification Search
CPC ............ A61M 2202/02; A61M 39/223; A61M 39/24; A61M 5/1782
See application file for complete search history.

(56) References Cited

U.S. PATENT DOCUMENTS

| | | | |
|---|---|---|---|
| 2004/0162515 A1 | 8/2004 | Chornenky et al. | |
| 2007/0106244 A1* | 5/2007 | Mosler | A61J 1/2096 604/411 |
| 2008/0142388 A1* | 6/2008 | Whitley | A61J 1/2096 206/438 |
| 2010/0218846 A1* | 9/2010 | Kriheli | A61J 1/2096 141/5 |
| 2010/0305507 A1* | 12/2010 | Duncan | A61M 5/14526 604/121 |
| 2013/0006212 A1* | 1/2013 | Garfield | A61J 1/2096 604/407 |

* cited by examiner

LIQUID TRANSFER SYSTEM

CROSS-REFERENCE TO RELATED APPLICATION/S

This application claims benefit from U.S. Provisional Patent Application No. 62/058,667 filed Oct. 2, 2014, the contents of which are incorporated herein by reference in their entirety.

FIELD AND BACKGROUND OF THE INVENTION

The present invention, in some embodiments thereof, relates to fluid transfer devices for use in medical and pharmacological applications, and more particularly, but not exclusively, to a system and a method for contamination-free transfer of liquids between containers.

Closed systems for handling drugs and closed system drug-transfer devices are well known in the art. They are typically used to reduce potential human exposure to drugs, particularly when transferring hazardous drugs from one receptacle to another. These types of systems and devices are generally designed to conform to the definitions provided by the American National Institute for Occupation Safety and Health (NIOSH) which is as follows:

"A closed system drug-transfer device (CSTD) is a drug transfer device that mechanically prohibits the transfer of environmental contaminants into the system and the escape of hazardous drug or vapor concentrations outside the system."

Exposure to hazardous drugs may cause serious health complications for those who are exposed to them, particularly when the exposure is over time. These complications may range from skin irritation, to birth defects, and even to development of various forms of cancer. For example, to prepare and administer chemotherapy drugs, which contain hazardous antineoplastic agents, the drugs need to be transferred from the original vial to a syringe and from a syringe to an IV infusion bag. Each transfer creates the possibility for exposure to the hazardous drugs.

Without using a CSTD, studies have shown hazardous drug residue on surfaces in the workplace, including on counters, and doorknobs, and even in unlikely places like a secretary's desk. This is due to the adhesive properties of the drugs. Using a CSTD, the rates of residue, as well as exposure to harmful vapors from the drugs, may be substantially reduced.

SUMMARY OF THE PRESENT INVENTION

There is provided, according to an embodiment of the present invention, a closed liquid transfer system including a transfer device including a multi-port manifold and a connector suitable to be attached to a drug container. The transfer device includes a first conduit to transfer a liquid entering an inlet port of the manifold through the connector and into the drug container, and a second conduit to transfer a gaseous fluid through the connector and the manifold to an outlet port of the manifold. The system additionally includes a tube connectable to the inlet port for transporting a liquid to the transfer device, and a tube connectable to the outlet port for transporting the gaseous fluid away from the transfer device.

According to an embodiment of the present invention, the system additionally includes a gas collection container to collect the gaseous fluid in the gas transporting tube.

According to an embodiment of the present invention, the manifold includes a hermetic seal in the outlet port to prevent liquid flow into the gas transporting tube.

According to an embodiment of the present invention, the system additionally includes a valve with three ports operable to allow unidirectional liquid flow from a first port to a second port, and from the second port to a third port.

According to an embodiment of the present invention, the system additionally includes a liquid supply tube connectable to the first port to transport the liquid into the first port.

According to an embodiment of the present invention, the liquid transporting tube is connectable to the third port of the valve.

According to an embodiment of the present invention, the system additionally includes a liquid container connectable to the liquid supply tube for supplying the liquid.

According to an embodiment of the present invention, the second port is connectable to any one of a manually operable syringe, an automatic syringe device, and a repeater pump.

According to an embodiment of the present invention, the second port includes a luer connector.

According to an embodiment of the present invention, the system additionally includes a unidirectional valve connected to the gaseous fluid transporting tube to allow unidirectional flow of the gaseous fluid towards the gas collection container.

According to an embodiment of the present invention, the drug container is any one of a drug vial or a drug bag.

According to an embodiment of the present invention, the liquid is a diluent.

There is provided, according to an embodiment of the present invention, a method of reconstituting a dry drug or diluting a liquid drug in a plurality of drug containers. The method includes: (1) attaching to a drug container a transfer device including a multi-port manifold and a connector suitable to be attached to the drug container, transfer device including a first conduit to transfer a liquid entering an inlet port of the manifold through the connector and into the drug container, and a second conduit to transfer a gaseous fluid through the connector and the manifold to an outlet port of the manifold; (2) administering a measured amount of a diluent into a tube connected to the inlet port of the manifold; (3) collecting in a gas collection container through a tube connected to the outlet port gaseous fluid expelled from the drug container; and (4) repeating the above steps for the plurality of drug containers.

According to an embodiment of the present invention, the method additionally includes administering the measured amount of diluent using any one of a syringe, an automatic syringe device, and a repeater pump.

According to an embodiment of the present invention, the method additionally includes supplying the diluent from a diluent container.

There is provided, according to an embodiment of the present invention, a transfer device for use in reconstituting dry drugs and for diluting liquid drugs in drug containers, the transfer device including a multi-port manifold and a connector suitable to be attached to a drug container, a first conduit to transfer a liquid entering an inlet port of the manifold through the connector and into the drug container; and a second conduit to transfer a gaseous fluid through the connector to an outlet port of the manifold.

BRIEF DESCRIPTION OF THE DRAWINGS

Some embodiments of the invention are herein described, by way of example only, with reference to the accompanying drawings. Details shown are for exemplary purposes and serve to provide a discussion of embodiments of the invention. The description and the drawings may be apparent to those skilled in the art how embodiments of the invention may be practiced.

DETAILED DESCRIPTION OF THE PRESENT INVENTION

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Drug reconstitution or dilution processes which use known CSTDs frequently involve many steps. A typical CSTD reconstitution or dilution process may include (a) connecting an adapter to a container holding a diluent (e.g. Saline, Dextrose, distilled water), for example a spike adapter connected to a Saline bag; (b) connecting a syringe to the adapter; (c) drawing an amount of diluent into the syringe; (d) removing the syringe from the diluent container and connecting it to an adaptor on a drug container (e.g. vial adaptor on a vial, or a spike adaptor on a bag); (e) injecting the diluent into the drug container holding a dry drug to be reconstituted or a fluid drug to be diluted; and (f) following injection of the diluent, depending on the CSTD, the syringe may be removed and steps b-e repeated for a new drug container using the same syringe, or alternatively, the syringe is discarded and a new syringe is used. The syringe may be fitted with a special connector which may fit onto a special adaptor on the drug container, both the connector and the adapter designed to prevent gases from escaping from the drug container (and the attached syringe) into the surrounding, and to prevent contaminated air from flowing into the drug container (and the attached syringe) from the surrounding.

The Applicant has realized, as may be appreciated from the above description, that drug reconstitution and drug dilution using known CSTDs may be tedious, time consuming, and potentially expensive processes, particularly when many drug containers have to be prepared. Known CSTDs may be practical for preparation of small quantities of drug containers, for example, a few containers per day as may be required by small size medical facilities, but may prove to be impractical for medium size and large size facilities where daily preparation requirements may exceed the tens, and something the hundreds, or even more.

The Applicant has further realized that reducing the number of steps in a typical CSTD reconstitution or dilution process may potentially overcome some, if not all of these drawbacks, and that a possible solution may be provided by a closed system liquid transfer system which may allow transferring of diluent from the diluent container to a plurality of drug containers without having to physically connect and disconnect a syringe to and from the diluent container and the drug container every time a new drug container is used.

In U.S. Pat. No. 8,196,614, 8,267,127, Israel Patent Application IL224630, and Israel Patent Application 226281, all commonly owned by the assignee of the present invention and incorporated herein by reference in their entirety, disclosed are embodiments of closed system liquid transfer devices suitable to provide contamination-free transfer of hazardous drugs. The Applicant has realized that some of these liquid transfer devices include connectors and adapters (e.g. spike adapters and vial adapters) which may be used with the closed system liquid transfer system of the present invention (hereinafter referred to as "liquid transfer system" for convenience) to allow economically preparing, with relative ease, measured quantities of contamination-free reconstituted or diluted drugs in a plurality of containers.

The Applicant has further realized that safety issues and potential hazards associated with reconstituting and diluting hazardous drugs may be remedied by using the liquid transfer system. For example, to reconstitute widely used hazardous drugs for chemotherapy such as Cyclophosphamide from their powder form to their injectable liquid form, a diluent such as a solution of sodium chloride (Saline) may be injected into a glass vial. Saline solution is typically available in infusion bags and generally needs to be drawn from the bag into a syringe. A 2 gram Cyclophosphamide vial typically requires the injection of 100 ml of solution. Since it may take a long time until the Cyclophosphamide powder dissolves in practice, many pharmacies may reconstitute a large number of such vials at once and use them throughout a work week to avoid long preparation times. The addition of the 100 ml of liquid into the vial may pose a safety issue and a potential safety hazard as the pressure in the glass vial increases (due to the addition of the diluent), possibly resulting in the reconstituted drug leaking out of the pressurized vial while stored for use. The liquid transfer system provides a solution to eliminate such overpressure conditions inside the vials and may provide leak-free transfer of fluids in a closed system.

The following figures illustrate exemplary embodiments of the liquid transfer system of the present invention, and an exemplary method of using the system for drug reconstitution and drug dilution. These figures and their associated description are not intended to be exhaustive or to limit the present invention to the disclosed embodiment.

The ordinary person skilled in the art may readily realize that the present invention may be practiced with modifications, substitutions, changes, and equivalents which are not disclosed herein yet are within the constraints of the teachings of the present invention. Furthermore, the skilled person may readily realize that the present invention may be used in other applications other than drug reconstitution and dilution as disclosed herein, for example, for contamination-free transferring of a measured amount of a liquid from a first container to a second container. In some cases the liquid may include a drug or combination of drugs being transferred from a first container to a second container, although any liquid which may be transferrable by means of a syringe may be suitable.

Figure 1:
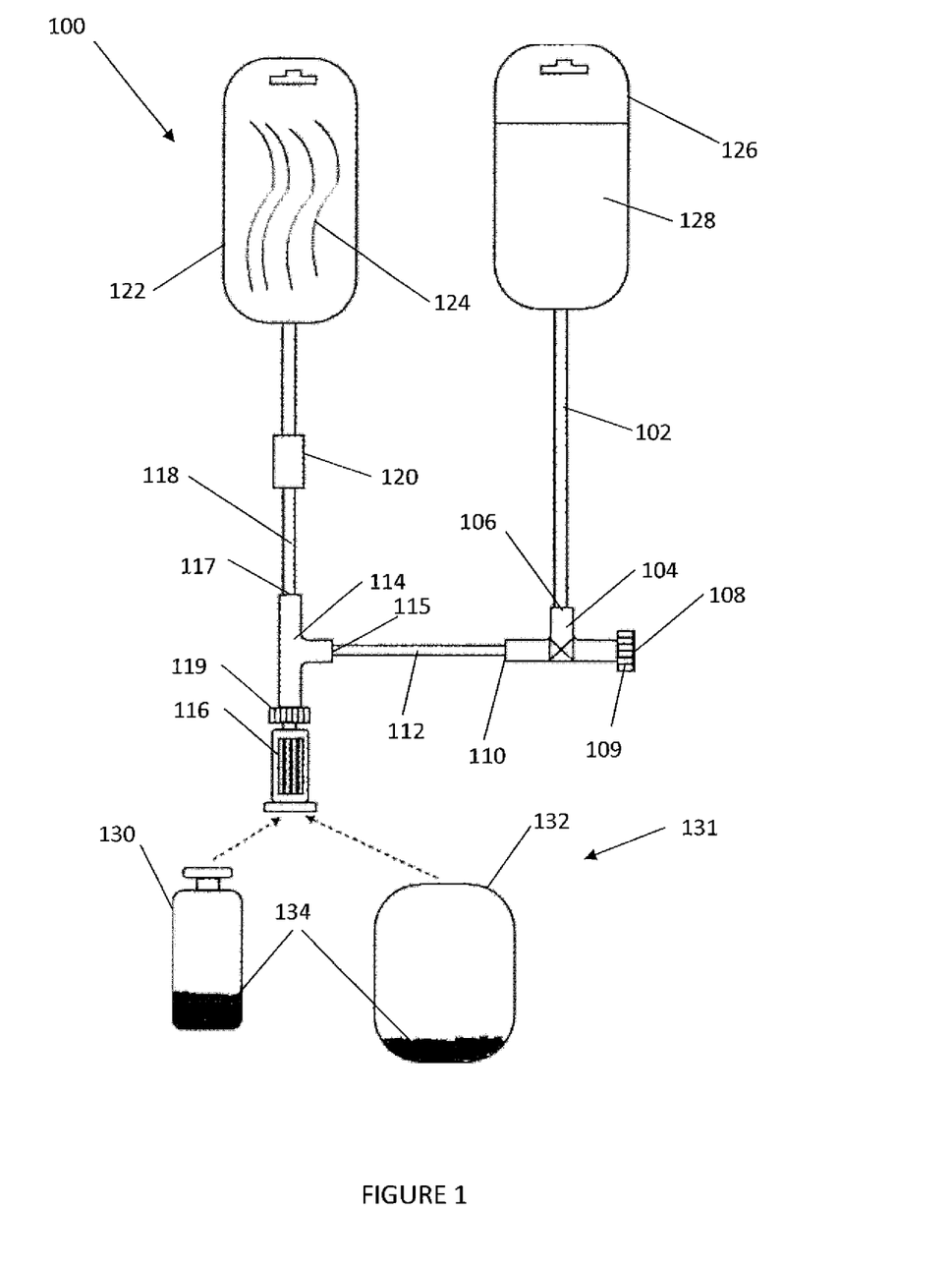
FIG. 1 schematically illustrates an exemplary liquid transfer system, according to an embodiment of the present invention.

Reference is now made to FIG. 1 which schematically illustrates an exemplary liquid transfer system 100, according to an embodiment of the present invention. Liquid transfer system 100 may include a liquid supply tube 102, a dual check valve 104 or functionally similar device, a liquid transport tube 112, a transfer device 101 including a multi-port manifold 114 and a CSTD connector 116, a gas transport tube 118, and a check valve 120 or functionally similar device. Additionally, liquid transfer system 100 may include a gas collection container 122. For convenience hereinafter, devices which are functionally similar to dual check valve 104 and to check valve 120 may also be referred to as "dual check valve 104" and "check valve 120", respectively.

In an embodiment of the present invention, liquid transfer system 100 may be used for contamination-free transfer of fluids, for example, a diluent 128, from a diluent container 126 to a drug container 131 which may be connected to CSTD connector 116, and to conduct gases 124 (which may include air mixed with drug-emitted vapors) from the drug container to gas collection container 122 in the closed system. Drug containers 131 may include a vial 130 or a bag drug container 132 containing a drug 134 which may be in dry form (for reconstitution) or liquid form (for dilution). These gases may be naturally pushed out of drug container 131 during the process of adding diluent 128 to drug 134 as the diluent takes up the space previously occupied by gases 124 in the drug container and there is no room for both.

Liquid supply tube 102 may connect at a distal end to diluent container 126 which may include one or more diluent bags containing diluent 128, which may for example, Saline, Dextrose, distilled water, or other type of fluids used to reconstitute dry drugs and/or to dilute fluid drugs. At a proximal end the liquid supply tube 102 may connect to dual check valve 104.

Dual check valve 104 may include three ports, a first port 106 which connects to liquid supply tube 102 and through which diluent 128 flows into the valve from diluent container 126, a second port 108 to which may be connected to a manually operated syringe, an automatically operated syringe, or a pump such as, for example a repeater pump, or any other source capable of injecting a measured amount of a fluid into the system, and a third port 110 to which may be connected a proximal end of liquid transport tube 112 and into which may flow diluent 128 from the dual check valve. Dual check valve 104 may allow unidirectional diluent flow from port 106 to port 108, and may further allow unidirectional flow from port 108 to port 110, as is described further on below with reference to FIGS. 3-5. Second port 108 may include a standard female luer lock port 109 or any other suitable connection means.

Liquid transport tube 112 may fluidly connect third port 110 in dual check valve 104 with multi-port manifold 114 to allow diluent flow from the dual check valve to the manifold. Multi-port manifold 114 may include a T-connector or a Y-connector and may include a first port 115 connecting to a distal end of liquid transport tube 112, a second port 119 which may connect to CSTD connector 116, and a third port 117 which may connect to a proximal end of gas transport tube 118 leading to gas container 122.

Figure 2:
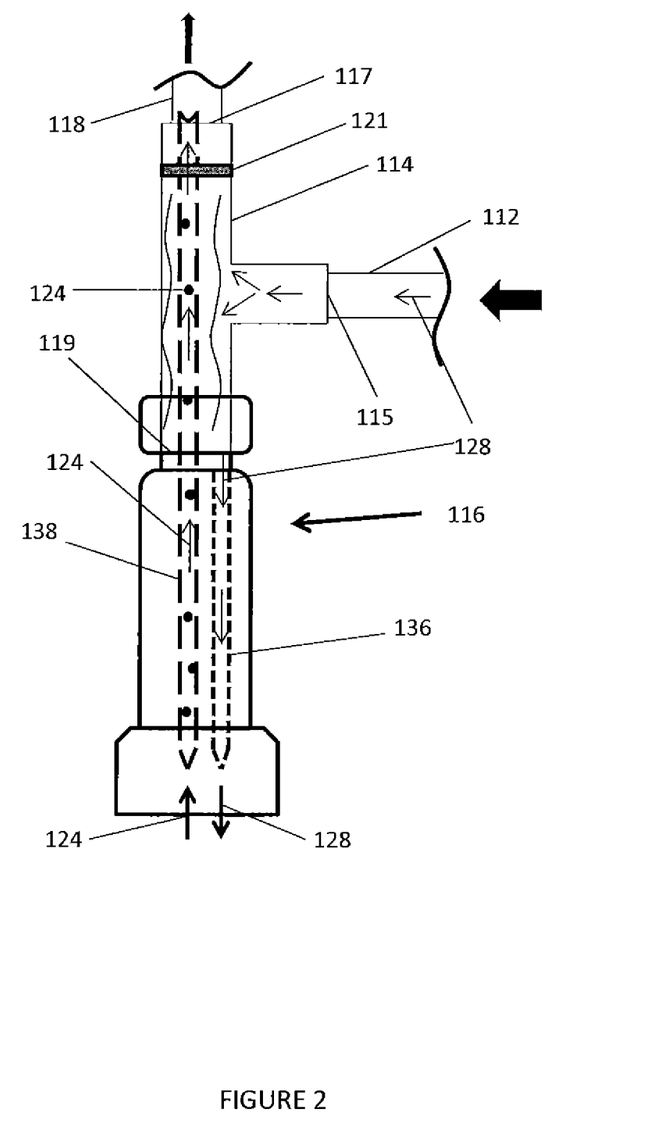
FIG. 2 schematically illustrates a detailed view of a transfer device including a multi-port manifold (T-connector) and a CSTD connector attached to a port of the manifold, according to an embodiment of the present invention.

Reference is now also made to FIG. 2 which schematically illustrates a detailed view of transfer device 101 including multi-port manifold 114 (T-connector) and CSTD connector 116 connected to second port 119, according to an embodiment of the present invention. Third port 117 in manifold 114 may include a seal 121 to prevent diluent 128 flowing into the manifold through first port 115 from flowing into gas transport tube 118.

CSTD connector 116 may include one of the connectors described in the aforementioned patents and patent applications commonly owned by the assignee of the present invention. The connectors described therein are suitable for use in CSTDs and attachable to adapters connectable to drug containers 131. The adapters may also include one of the adapters described in the aforementioned patents and patent applications commonly owned by the assignee of the present invention. For example, the CSTD connector 116 may be a syringe connector and the adapter a vial adapter for attaching to vial (drug container) 130, both as described in U.S. Pat. No. 8,196,614, the syringe connector appropriately modified to connect to second port 119 in manifold 114. Alternatively, the adapter may be a bag adapter for attaching to bag drug container 132 to which the modified syringe connector may be connected.

CSTD connector 116 may include a diluent conduit 136 through which diluent 128 entering first port 115 in manifold 114 may flow through the manifold and through the vial or bag adapter (not shown) into drug container 131. CSTD connector 116 may additionally include a gas conduit 138 through which gas 124 which may include air, which may be mixed with drug vapors, may flow from inside drug container 131 through the adapter and through the connector towards gas transport tube 118 and onwards to gas container 122. Gas conduit 138 may extend through CSTD connector 116 into manifold 114 and through seal 121 in third port 117 in a direction of gas transport tube 118.

In some embodiments, CSTD connector 116 and multi-port manifold 114 may be formed as a single component or may be preassembled in factory as a single assembly. Alternatively, CSTD connector 116 and multi-port manifold 114 may be two separate components which may be connected together as one assembly during in situ assembly of liquid transfer system, with provisions made in seal 121 to allow the insertion of gas conduit 138 through the seal.

Gas transport tube 118 may be connected at a proximal end to third port 117 of manifold 114 and may transport gas 124 flowing through gas conduit 138 from drug container 131 to gas container 122. Check valve 120 in gas transport tube 118 may allow unidirectional gas flow into the gas collection bag 122 and may prevent gas flow from the gas collection bag in a direction toward manifold 114. Check valve 120 may additionally prevent any liquid which may collect in gas collection bag 122, for example as a result of a wash-out procedure, from flowing out of the gas collection bag towards manifold 114.

It may be appreciated by the skilled person that the liquid transfer system of the present invention may be implemented based on the above description using different components or combinations of components and that the practice of the invention may not be limited to using the same exact components or component as shown and described with reference to FIG. 1. The following FIGS. 3-5 illustrate exemplary applications of liquid transfer system 100 with different mechanisms for injecting measured amounts of dilation 128 (or other fluid) into the system, according to some embodiments of the present invention.

Figure 3:
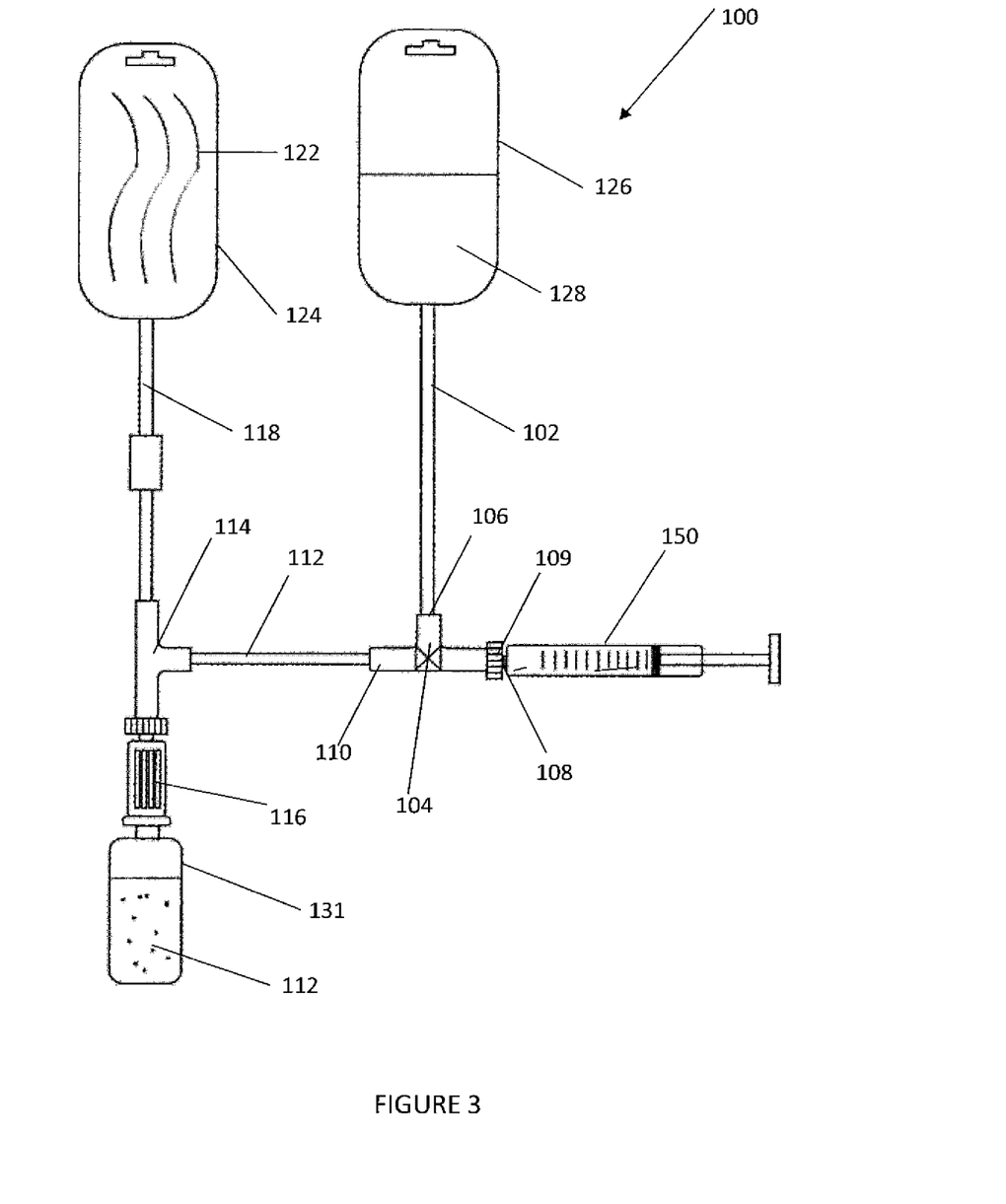
FIG. 3 illustrates the liquid transfer system used with a manually-operated syringe in a closed system reconstitution or dilation process, or otherwise liquid transfer process, according to an embodiment of the present invention.

FIG. 3 schematically illustrates liquid transfer system 100 used with a manually-operated syringe 150 in a closed system reconstitution or dilation process, or otherwise liquid transfer process, according to an embodiment of the present invention. Syringe 150 may be connected to luer connector 109 in second port 108 of dual check valve 104.

In operation, diluent 128 may flow from diluent container 126 through liquid supply tube 102 into port 106 in dual check valve 104 responsive to syringe 150 drawing of the diluent when the plunger is pulled. Diluent flow from port 106 is unidirectional into port 108 and diluent 128 may be drawn into syringe 150. An amount of diluent 128 drawn into syringe 150 may be determined by pulling the plunger until the desired position (as visually determined by the position of the plunger in relation to the markings on the syringe). Once filled with the desired amount of diluent 128, the plunger may be pushed forcing the measured amount of diluent 128 in syringe 150 to flow into port 108. Flow from port 108 may be unidirectional to third port 110 in dual check valve 104, so that, upon pushing of the plunger, the measured amount of diluent 128 flows through dual check valve 104 into liquid transport tube 112. From liquid transport tube 112, the measured amount of diluent 128 may flow into manifold 114 and through CSTD connector 116 through diluent conduit 136 into drug container 131 (vial container 130 or bag drug container 132) to produce the reconstituted (or diluted) drug 135. Gases 124 displaced from vial 130 may flow through gas conduit 138 in CSTD connector 116 and manifold 114 into gas transport tube 118 into gas collection bag 122.

Figure 4:
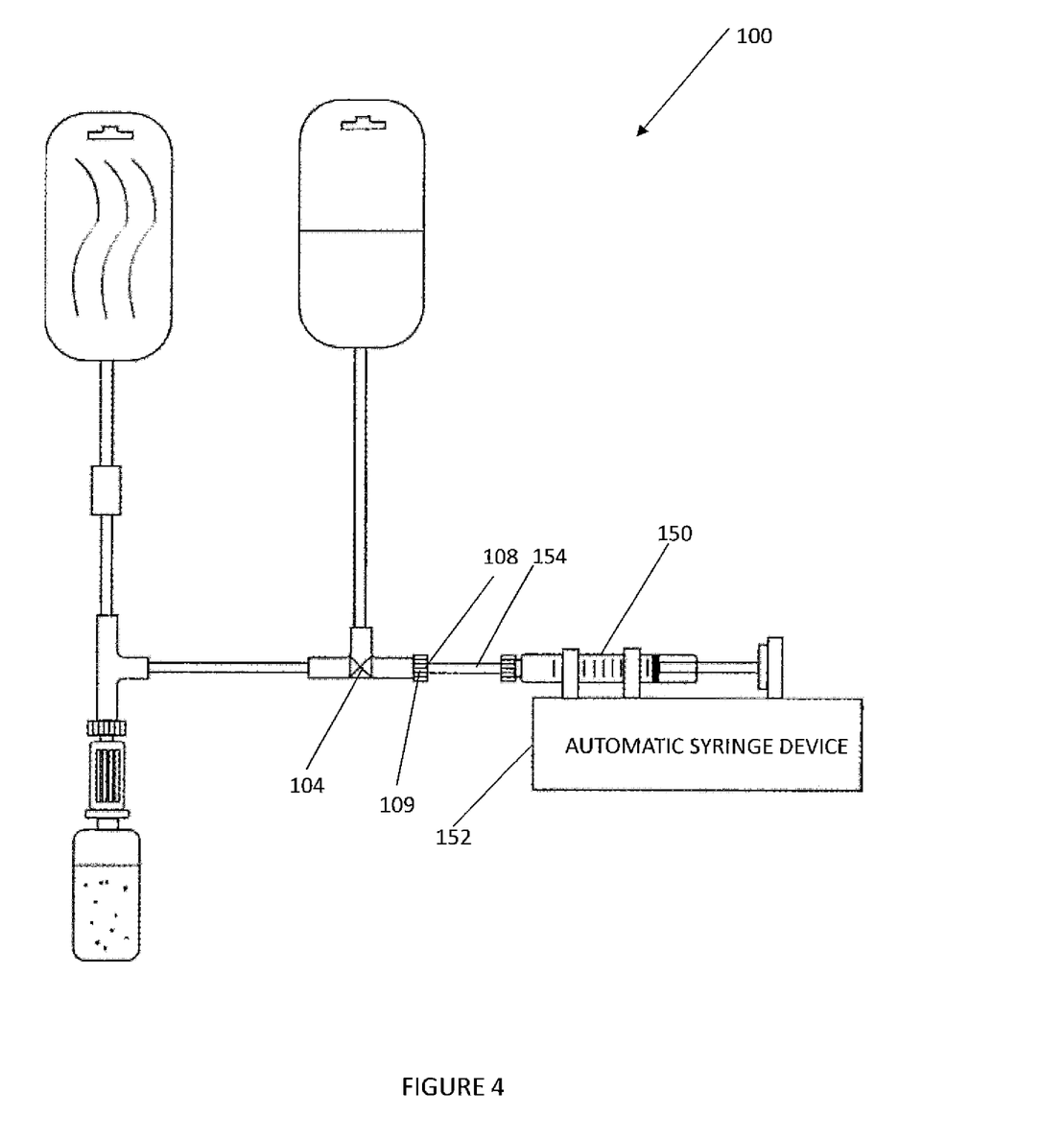
FIG. 4 illustrates the liquid transfer system used with an automatic syringe device in a closed system reconstitution or dilation process, or otherwise liquid transfer process, according to an embodiment of the present invention.
Figure 5:
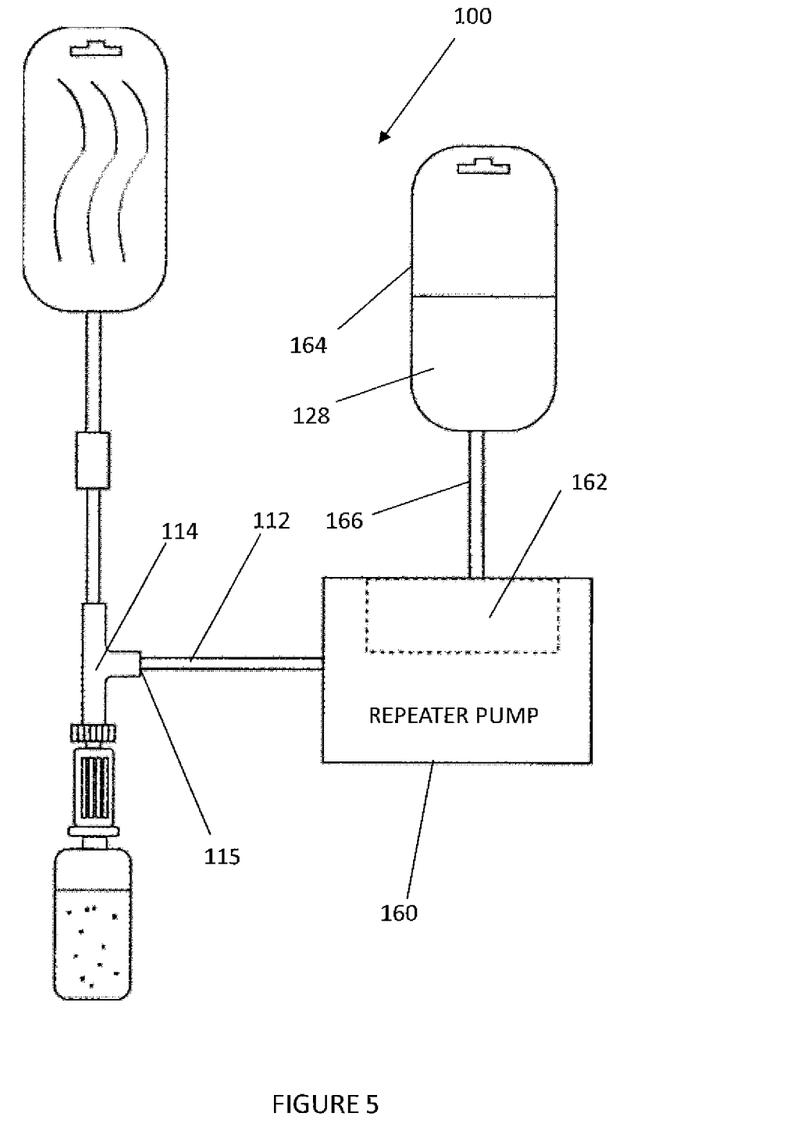
FIG. 5 illustrates the liquid transfer system used with a repeater pump in a closed system reconstitution or dilation process, or otherwise liquid transfer process, according to an embodiment of the present invention.

FIG. 4 schematically illustrates liquid transfer system 100 used with an automatic syringe device 152 in a closed system reconstitution or dilation process, or otherwise liquid transfer process, according to an embodiment of the present invention. Syringe 150 may be mounted on automatic syringe device 152 (may also be semi-automatic) and may be connected to second port 108 in dual check valve 104 by means of a transfer tube 154 through which diluent 128 may flow to and from the syringe. Alternatively, syringe 150 may be directly connected to luer connector 109 in second port 108. The operation of liquid transfer system 100 is substantially similar to that described for FIG. 3 with the exception that syringe operation is automatic (by means of automatic syringe device 152).

FIG. 5 schematically illustrates liquid transfer system 100 used with a repeater pump 160 in a closed system reconstitution or dilation process, or otherwise liquid transfer process, according to an embodiment of the present invention. Repeater pump 160, or other suitable automatic or semi-automatic fluid injection device, may include its own diluent container 162 or may be fluidly connected to an external diluent container 164 through a supply tube 166, so that diluent container 126 and liquid supply tube 102 may not be required. Liquid transport tube 112 may be directly connected to repeater pump 160 so that dual check valve 104 previously described may also not be required. Liquid transfer system 100 may operate with diluent 128 being injected from repeater pump 160 directly into port 115 in manifold 114. The operation of liquid transfer system 100 with a repeater pump 160 may be substantially similar to that described for FIG. 3 with the exception that diluent container 126, liquid supply tube 102, and dual check valve 104 are not required.

Figure 6:
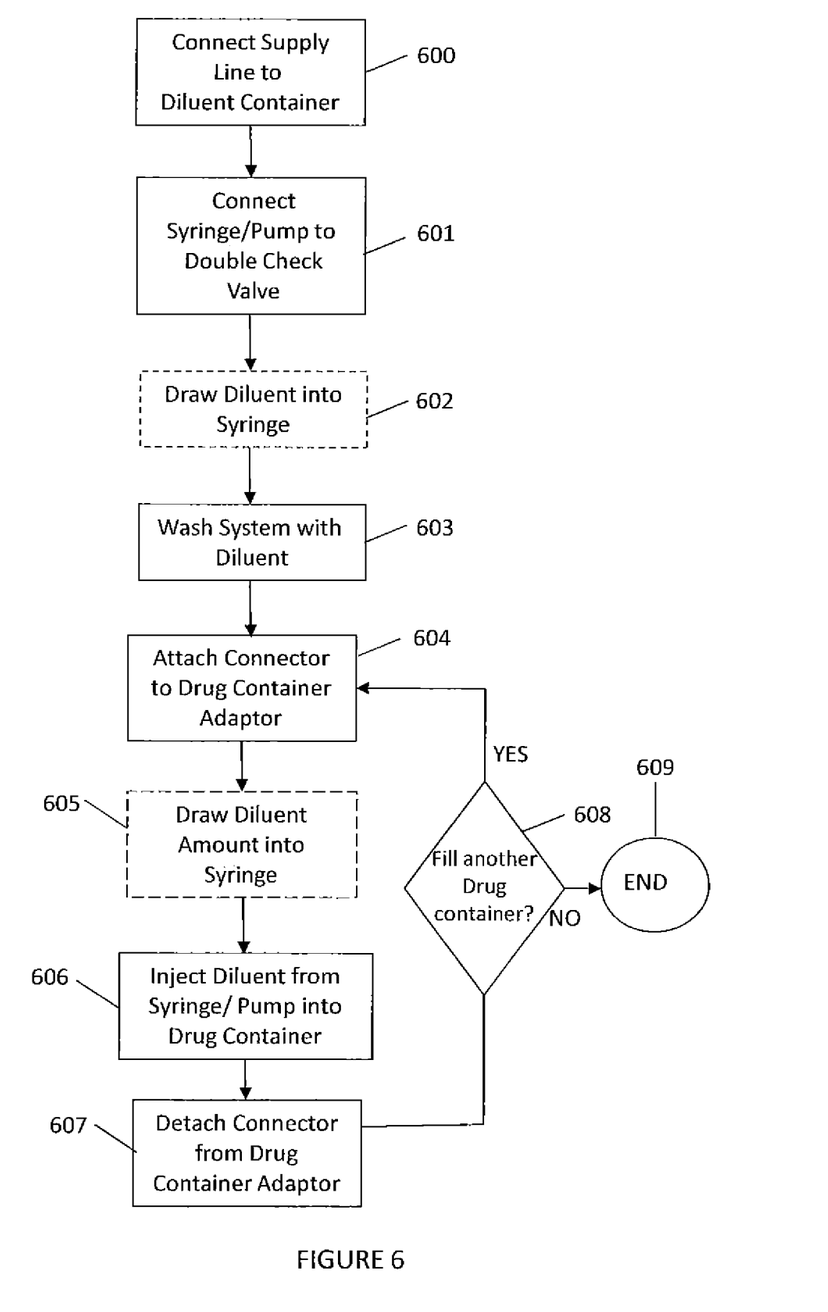
FIG. 6 which is a flow chart of an exemplary method of using closed system liquid transfer system for drug reconstitution or drug dilution in a plurality of drug containers, according to an embodiment of the present invention.

Reference is now made to FIG. 6 which is a flow chart of an exemplary method of using closed system liquid transfer system for drug reconstitution or drug dilution in a plurality of drug containers, according to an embodiment of the present invention. The method may include a first stage which includes setting up the liquid transfer system, and a second stage which includes liquid transfer to the plurality of drug containers following system setup. In describing the method, for clarity purposes, reference is made to liquid transfer system 100 described in FIGS. 1 and 3, although reference may also be made to the embodiments of FIGS. 4 and 5.

It may be apparent to the ordinary person skilled in the art that the method may be practiced with more or less steps, or with a different sequence of steps, and which may include adding and/or deleting steps, skipping steps, and rearranging the order of the steps.

First Stage

At 600, liquid supply tube 102 may be connected to diluent container 126. Diluent container 126 may be a diluent bag or other suitable container for holding diluent 128. Diluent container 126 may be prefitted with an adapter connectable to liquid supply tube 102 or alternatively, the adapter may be connected to the container during this step.

At 601, syringe 150 is connected to second port 108 of double check valve 104. Syringe 150 may be a manually operated syringe or may be mounted on an automatic syringe device 152. Alternatively, instead of the syringe (manual or automatic), a repeater pump 160 or other suitable injection means may be connected to port 108 (or alternatively directly to liquid transport tube 112).

At 602, diluent 128 is drawn into syringe 150 by pulling the plunger. An amount of diluent shall be sufficient for flushing out and priming the system in order to push the air out and replace it with liquid and also to wash out possible drug residue on any of the system components. Alternatively, if repeater pump is used 160, then there is no need to draw the diluent from the diluent container 126 which may not be required at all, rather the repeater pump may pump from optional pump container 162 or from external diluent container 164 a required amount for flushing and priming (see 604).

At 603, diluent 128 is injected into liquid transport tube 112 to flush out the system. As part of the flushing process, diluent 128 may flow through multi-port manifold 114 to CSTD connector 116 and into diluent conduit 136. CSTD connector 116 is not connected in this step to the vial adaptor so diluent 128 may flow from diluent conduit 136 through a chamber in the CSTD connector into gas conduit 138 (i.e. the CSTD connector may be functionally similar to connector section 25 in U.S. Pat. No. 8,196,614). Diluent 128 flowing into gas conduit 138 may flow out into gas transport 118 and into the gas container 122 where it is collected and contained.

Second Stage

At 604, drug container 131 with an attached adapter (e.g. vial 130 with an attached vial adapter or bag 132 with an attached spike adapter) is connected to CSTD connector 116. The following 606 may be interchangeable with this 605.

At 605, a required amount of diluent 128 to be used for reconstitution or dilution is drawn into syringe 150 from diluent container 126. The amount may be measured by a user on the syringe scale while pulling the plunger (to draw the diluent into the syringe) or may be based on other parameters (for example, plunger pulling length) for automatic syringed device 150. Alternatively, instead of the syringe (manual or automatic), repeater pump 160 may be used and drawing of diluent 128 is not required. Repeater pump 160 may inject (see 607) a preprogrammed, required amount.

At 606, diluent 128 is injected into liquid transport tube 112 by pushing on the plunger or injected by the pump. The diluent may flow through liquid transport tube 112 into multi-port manifold 114 and through diluent conduit 136 in the manifold and CSTD connector 116 through the adapter into drug container 131. Gas 124 in drug container 131 may flow out through gas conduit 138 into the gas transport tube 118 and thereto into gas container 124. Seal 121 in multi-port manifold 114 may prevent the injected diluent from flowing out the multi-port manifold into gas transport tube 118.

At 607, following diluent 128 having been injected into drug container 131, the adapter (with the drug container attached) may be disconnected from CSTD connector 116.

At 608, if a same drug 134 in another ("new") drug container 131 is to be reconstituted or diluted, the fifth through eighth steps may be repeated. Similarly if the diluent container 126 is replaced by a diluent container with the same diluent. If a different drug is to be reconstituted or diluted, or a new type of diluent is to be used, the first to eighth steps may be repeated.

At 609, once all drug containers 131 have been filled, the process ends.

The foregoing description and illustrations of the embodiments of the invention has been presented for the purposes of illustration. It is not intended to be exhaustive or to limit the invention to the above description in any form.

Any term that has been defined above and used in the claims, should to be interpreted according to this definition.

The reference numbers, when included in the claims, are not a part of the claims, but rather used for facilitating the reading thereof. These reference numbers should not be interpreted as limiting the claims in any form.

The invention claimed is:

1. A closed liquid transfer system comprising:
   a transfer device for use in reconstituting drugs in a plurality of drug containers, each drug container of the plurality of drug containers including an adapter, said transfer device comprising;
      a multi-port manifold and a connector suitable to be removably attached to the adapter on one of said plurality of drug containers, said transfer device further comprising:
      a first conduit to transfer a liquid from an inlet port of said manifold through said connector and into the attached drug container, and
      a second conduit to transfer a gaseous fluid from inside said attached drug container through said connector and said manifold to an outlet port of said manifold;
   a liquid transporting tube connected to said inlet port for transporting a liquid to said transfer device;
   a gas transporting tube connected to said outlet port for transporting said gaseous fluid from said attached container away from said transfer device;
   a gas collection container to collect said gaseous fluid from each drug container; and
   a unidirectional valve connected to said gas transporting tube to allow unidirectional flow of said gaseous fluid towards said gas collection container.

2. A system according to claim 1 wherein said adapter is a drug vial adapter or a drug bag adapter.

3. A system according to claim 1 wherein said manifold comprises a hermetic seal in said outlet port to prevent liquid flow into said gas transporting tube.

4. A system according to claim 1 further comprising a valve with three ports operable to allow unidirectional liquid flow from a first port to a second port, and from said second port to a third port.

5. A system according to claim 4 further comprising a liquid supply tube connectable to said first port to transport said liquid into said first port.

6. A system according to claim 4 wherein said liquid transporting tube is connectable to said third port of said valve.

7. A system according to claim 5 further comprising a liquid container connectable to said liquid supply tube for supplying said liquid.

8. A system according to claim 4 wherein said second port is connectable to any one of a manually operable syringe, an automatic syringe device, and a repeater pump.

9. A system according to claim 4 wherein said second port comprises a luer connector.

10. A system according to claim 1 wherein said drug container is any one of a drug vial or a drug bag.

11. A system according to claim 1 wherein said liquid is a diluent.

12. A method of reconstituting a dry drug or diluting a liquid drug in a plurality of drug containers, the method comprising:
    using a transfer device for use in reconstituting drugs in the plurality of drug containers, each drug container of the plurality of drug containers including an adapter, said transfer device comprising a multi-port manifold and a connector suitable to be removably attached to the adapter on one of said plurality of drug containers, and further comprising a first conduit to transfer a liquid from an inlet port of said manifold through said connector and into the attached drug container, and a second conduit to transfer a gaseous fluid from inside said attached drug container through said connector and said manifold to an outlet port of said manifold, performing the steps of:
    (a) attaching the adapter of a first drug container to said connector;
    (b) administering a measured amount of a diluent into said first drug container through a liquid transporting tube connected to said inlet port of said manifold and through said first conduit;
    (c) collecting a gaseous fluid expelled from said first drug container in a gas collection container through a gas transporting tube connected to said outlet port and a unidirectional valve connected to said gas transporting tube to allow unidirectional flow of said gaseous fluid towards said gas collection container;
    (d) detaching the adapter of said first drug container from said transfer device; and
    (e) repeating the above steps (a) to (d) for each drug container in said plurality of drug containers.

13. A method according to claim 12 further comprising administering said measured amount of diluent using any one of a syringe, an automatic syringe device, and a repeater pump.

14. A method according to claim 12 further comprising supplying said diluent from a diluent container.

15. A method according to claim 12 wherein said adaptor is a drug vial adaptor.

16. A method according to claim 12 wherein said adaptor is a drug bag adaptor.

17. A transfer device for use in reconstituting dry drugs and for diluting liquid drugs in a plurality of drug containers, each drug container including an adapter, the transfer device comprising:
- a multi-port manifold and a connector suitable to be removably attached to the adapter on one of said plurality of drug containers;
- a first conduit to transfer a liquid from an inlet port of said manifold through said connector and into the attached drug container, said inlet port connectable to a liquid transporting tube for transporting a liquid to the transfer device;
- and a second conduit to transfer a gaseous fluid from inside said attached drug container through said connector to an outlet port of said manifold, said outlet connectable to a gas transporting tube for transporting said gaseous fluid from said attached container to a gas collection container, said gas transporting tube connected to a one-way valve to allow unidirectional flow of said gaseous fluid towards said gas collection container.

18. A transfer device according to claim 17 wherein said adaptor is a drug vial adaptor.

19. A transfer device according to claim 17 wherein said adaptor is a drug bag adaptor.

* * * * *